US012594010B2

(12) United States Patent
Yang et al.

(10) Patent No.: US 12,594,010 B2
(45) Date of Patent: Apr. 7, 2026

(54) MINIMALLY INVASIVE SKIN PATCH, METHOD OF MANUFACTURING SAME, AND BLOOD GLUCOSE MEASURING APPARATUS USING SAME

(71) Applicant: ELECTRONICS AND TELECOMMUNICATIONS RESEARCH INSTITUTE, Daejeon (KR)

(72) Inventors: Hoe Sung Yang, Daejeon (KR); Kang Bok Lee, Daejeon (KR); Kwang Soo Cho, Daejeon (KR); Kyu Won Han, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 284 days.

(21) Appl. No.: 17/511,506

(22) Filed: Oct. 26, 2021

(65) Prior Publication Data

US 2022/0125351 A1 Apr. 28, 2022

(30) Foreign Application Priority Data

Oct. 27, 2020 (KR) ......................... 10-2020-0140230
Sep. 8, 2021 (KR) ......................... 10-2021-0119771

(51) Int. Cl.
*A61B 5/00* (2006.01)
*A61B 5/145* (2006.01)

(52) U.S. Cl.
CPC .......... *A61B 5/14532* (2013.01); *A61B 5/685* (2013.01)

(58) Field of Classification Search
CPC ............................ A61B 5/14532; A61B 5/685
See application file for complete search history.

(56) References Cited

U.S. PATENT DOCUMENTS

| | | | |
|---|---|---|---|
| 8,306,593 B2 | 11/2012 | Hwang et al. | |
| 10,251,584 B2 | 4/2019 | Jin et al. | |
| 10,278,622 B2 | 5/2019 | Arko et al. | |
| 11,360,107 B1 * | 6/2022 | Young ................ | G01N 35/1016 |

(Continued)

FOREIGN PATENT DOCUMENTS

| | | | |
|---|---|---|---|
| EP | 2308365 B1 | 11/2014 | |
| JP | 2006521555 A | 9/2006 | |

(Continued)

*Primary Examiner* — Alex M Valvis
*Assistant Examiner* — Grace L Rozanski
(74) *Attorney, Agent, or Firm* — Rabin & Berdo, P.C.

(57) ABSTRACT

In the invention, only light reflected by a portion in which a microneedle is disposed arrives on a photodetector, and light reflected by a portion in which the microneedle is not disposed does not arrive on the photodetector. Disclosed is a skin patch for measuring blood glucose including a patch including a skin attachment surface, a reaction layer which reacts with glycation products of skin, and a plurality of microneedles disposed on the skin attachment surface to guide the glycation products of the skin to the reaction layer and an optical trap which allows light, which is reflected by only one portion among a portion in which the microneedle is disposed and a portion in which the microneedle is not disposed when the light is emitted to the reaction layer, to pass therethrough, a method of manufacturing the same, and a blood glucose measuring apparatus using the same.

10 Claims, 3 Drawing Sheets

(56) References Cited

U.S. PATENT DOCUMENTS

| | | | | |
|---|---|---|---|---|
| 2011/0224515 A1* | 9/2011 | Mir | .................... | A61B 5/15151 |
| | | | | 600/317 |
| 2018/0078513 A1* | 3/2018 | Ueno | .................... | A61M 37/00 |
| 2018/0177439 A1* | 6/2018 | Sia | ........................ | A61L 31/048 |
| 2019/0151639 A1 | 5/2019 | Mou et al. | | |
| 2019/0159705 A1 | 5/2019 | Sim et al. | | |
| 2021/0205632 A1* | 7/2021 | Xu | ........................ | A61N 5/0601 |
| 2021/0386373 A1* | 12/2021 | Kendall | .............. | A61B 5/6839 |

FOREIGN PATENT DOCUMENTS

| | | | |
|---|---|---|---|
| JP | 2007216030 A | 8/2007 |
| JP | 2019093125 A | 6/2019 |
| KR | 100694598 B1 | 3/2007 |
| KR | 100871074 B1 | 11/2008 |
| KR | 101661287 B1 | 9/2016 |
| KR | 101716663 B1 | 3/2017 |
| KR | 101964025 B1 | 3/2019 |
| KR | 1020190063446 A | 6/2019 |
| KR | 1020190093442 A | 8/2019 |
| KR | 20200042312 A | 4/2020 |
| KR | 20210001067 A | 1/2021 |
| KR | 20210063818 A | 6/2021 |

* cited by examiner

MINIMALLY INVASIVE SKIN PATCH, METHOD OF MANUFACTURING SAME, AND BLOOD GLUCOSE MEASURING APPARATUS USING SAME

CROSS-REFERENCE TO RELATED APPLICATIONS

This application claims the benefit under 35 USC § 119 a of Korean Patent Applications, No. 10-2020-0140230, filed on Oct. 27, 2020 and No. 10-2021-0119771, filed on Sep. 8, 2021 in the Korean Intellectual Property Office, the entire disclosures of which are incorporated herein by reference for all purposes.

BACKGROUND

1. Field of the Invention

The present invention relates to a microneedle skin patch for measuring blood glucose through minimal invasion and a blood glucose measuring apparatus using the same, and specifically, relates to minimizing an error by uniformly measuring a degree of change in enzyme of a patch which is changed by glycation products.

2. Discussion of Related Art

Since the conventional blood glucose measuring apparatus uses a method of measuring blood glucose from blood collected by pricking skin using a needle in order to measure glycation end products such as blood glucose, there is a problem of causing pain and fear of a patient.

In addition, in another method of minimally invasive measuring using a microneedle skin patch, there is a difference in enzymatic reaction for measuring between a microneedle portion which minimally invades skin and a portion which does not invade the skin. When the patch is used, light is emitted to an enzymatic reaction part, and a physical quantity of the light reflected by the enzymatic reaction part is measured to calculate a blood glucose.

However, since light reflected by the microneedle portion which invades the skin and light reflected by the portion which does not invade the skin are mixed and detected by a photodetector, an accurate degree of enzymatic reaction is not measured.

SUMMARY OF THE INVENTION

The present invention is directed to reducing a blood glucose measurement error by uniformly measuring a change in enzymatic reaction of a minimally invasive microneedle skin patch.

In a minimally invasive skin patch and a blood glucose measuring apparatus using the same, only light reflected by a portion in which a microneedle is disposed arrives on a photodetector, and light reflected by a portion in which the microneedle is not disposed does not arrive on the photodetector.

Specifically, according to one aspect of the present invention, there is provided a skin patch for measuring blood glucose including a patch including a skin attachment surface, a reaction layer which reacts with glycation products of skin, and a plurality of microneedles disposed on the skin attachment surface to guide the glycation products of the skin to the reaction layer; and an optical trap which allows light, which is reflected by only one portion among a portion in which the microneedle is disposed and a portion in which the microneedle is not disposed when the light is emitted to the reaction layer, to pass therethrough.

According to another aspect of the present invention, there is provided a method of manufacturing a skin patch for measuring blood glucose, the method including manufacturing a patch by forming a skin attachment surface and a reaction layer which reacts with glycation products of skin and attaching a plurality of microneedles to the skin attachment surface to guide the glycation products of the skin to the reaction layer, manufacturing an optical trap which allows light, which is reflected by only one portion among a portion in which the microneedle is disposed and a portion in which the microneedle is not disposed when the light is emitted to the reaction layer, to pass therethrough, and arranging the optical trap on the reaction layer of the patch.

In the above, the optical trap may include a light passing part (e.g., transparent part) which allow light reflected by the portion, in which the microneedle is disposed, to pass therethrough and may include a light blocking part (e.g., opaque part) which block light reflected by the portion in which the microneedle is not disposed. Or, conversely, the optical trap may include a light blocking part which blocks light reflected by the portion in which the microneedle is disposed and a light passing part which allow light reflected by the portion in which the microneedle is not disposed to pass therethrough.

According to still another aspect of the present invention, there is provided a blood glucose measuring apparatus using the above-mentioned skin patch for measuring blood glucose. The apparatus may include a reaction detector which emits light to a reaction layer of the patch and receives light reflected by the reaction layer to detect reactivity of glycation products.

The structures and the operations of the present invention will be clearer due to specific embodiments which will be described below with reference to the accompanying drawings.

BRIEF DESCRIPTION OF THE DRAWINGS

The above and other objects, features, and advantages of the present invention will become more apparent to those of ordinary skill in the art by describing exemplary embodiments thereof in detail with reference to the accompanying drawings, in which.

DETAILED DESCRIPTION OF EXEMPLARY EMBODIMENTS

Advantages and features of the present invention and methods of achieving the same will be clearly understood with reference to the following exemplary embodiments described in detail with the accompanying drawings. However, the present invention is not limited to the embodiments to be disclosed below and may be implemented in various different forms. The embodiments are provided only in order to fully describe the present invention and fully notify those skilled in the art of the scope of the present invention, and the scope of the present invention is defined by the appended claims. In addition, the terms used herein are provided only to describe the embodiments of the present invention and are not for purposes of limitation. Unless the context clearly indicates otherwise, the singular forms described in the specification include the plural forms. In addition, the terms "comprise," or "comprising," used herein are used as a meaning of specifying some stated components, steps, operations and/or elements but do not preclude the presence or addition of one or more other components, steps, operations and/or elements. Hereinafter, the exemplary embodiments of the present invention will be described in detail with reference to the accompanying drawings. When the embodiments are described, in a case in which specific descriptions of related known components or functions obscure the gist of the present invention, the specific descriptions will be omitted.

First, a general minimally invasive microneedle skin patch will be described briefly.

Figure 1:
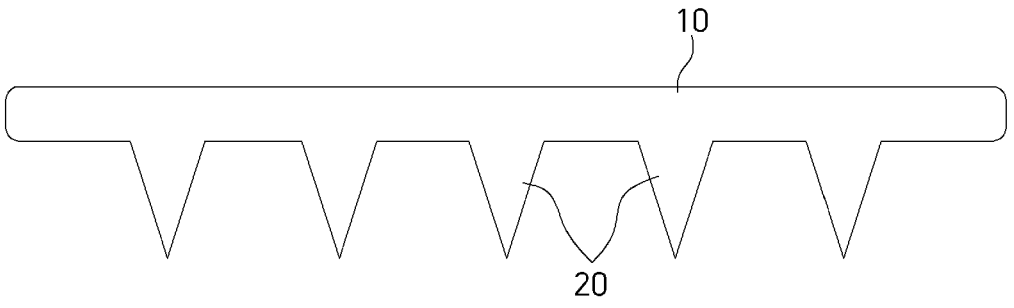
FIG. 1 is a schematic side view illustrating a general minimally invasive microneedle skin patch.

FIG. 1 is a schematic side view illustrating a microneedle patch. A plurality of microneedles 20 are attached to a lower surface of the patch 10. The minimally invasive microneedle skin patch of FIG. 1 may be formed of composite materials or may have a multilayered structure.

Figure 2A:
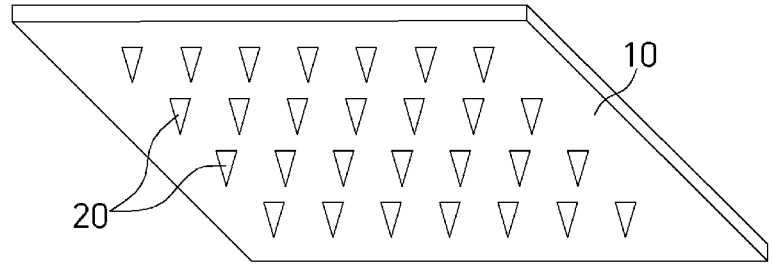
FIG. 2A is a bottom view of the patch shown in FIG. 1, on which microneedles are disposed.
Figure 2B:
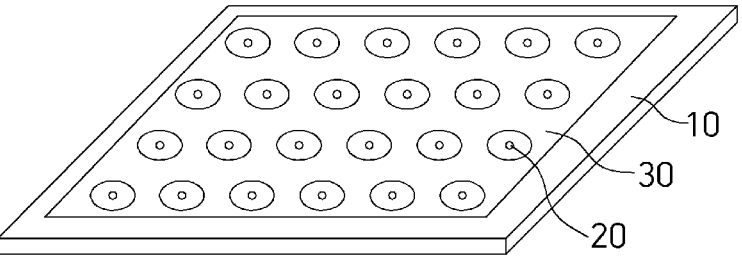
FIG. 2B is a top view of the patch.

FIG. 2A is a bottom view of the patch shown in FIG. 1, on which the microneedles are disposed, and FIG. 2B is a top view of the patch. In FIG. 2B, it may be seen that a reaction layer 30 which may enzymatically react with the glycation products is formed in the patch 10.

Figure 3:
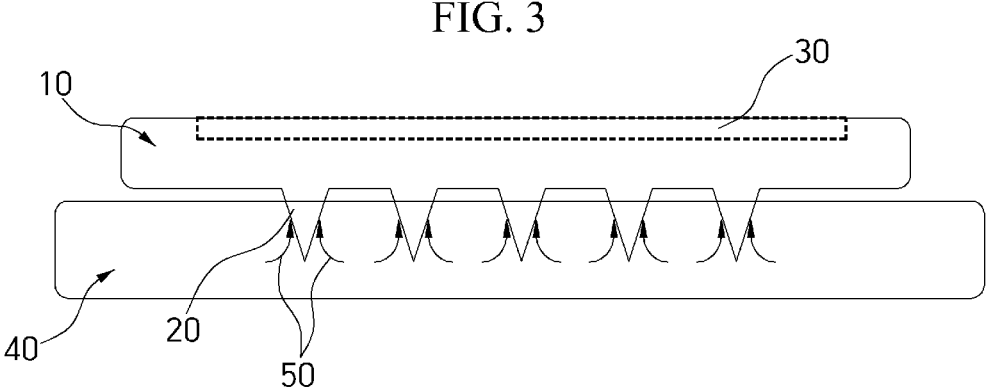
FIG. 3 is a view illustrating a process in which, when the patch (10) is attached to skin (40), glycation products (50) are absorbed into the patch (10) from the skin (40) through the microneedles (20)

FIG. 3 is a view illustrating a process in which, when the patch 10 is attached to skin 40, glycation products 50 start to be absorbed into the patch 10 from the skin 40 through the microneedles 20.

Figure 4:
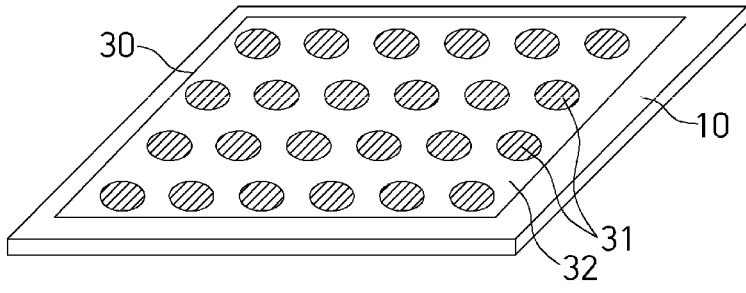
FIG. 4 is a top view illustrating a reaction layer (30) which has enzymatically reacted with the glycation products (50)

FIG. 4 is a top view illustrating the reaction layer 30 which has enzymatically reacted with the glycation products (50). Here, there is a difference in reactivity of the enzymatic reaction occurring in the patch between portions 31 in which the microneedles are disposed and portions 32 in which the microneedles are not disposed. In FIG. 4, a concentration of a reactant in the portion 31 in which the microneedle 20 is disposed is expressed to be darker than a concentration of the reactant in the portion 32 in which the microneedle is not disposed. However, a concentration distribution may also be reversed according to an enzymatic reactant.

Figure 5:
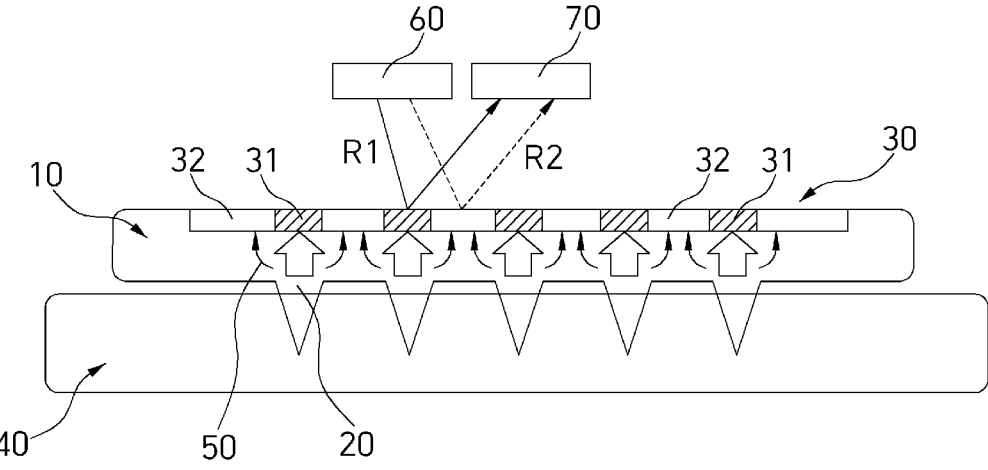
FIG. 5 is a view illustrating a light source (60) and a photodetector (70) which are provided to detect a difference in reactant concentration occurring when the glycation products (50) absorbed into the patch (10) react with the reaction layer (30) at different reactivities as in FIG. 4.

FIG. 5 is a view illustrating a light source 60 and a photodetector 70 which are provided as a reaction detector to detect a difference in reactant concentration occurring when the glycation products 50 absorbed into the patch 10 react with the reaction layer 30 at different reactivities as in FIG. 4. Light emitted from the light source 60 is reflected by the portion 31 in which the microneedle is disposed and reflected by the portion 32 in which the microneedle is not disposed at different physical quantities (for example, reflectivity), and reflected light R1 and reflected light R2 are detected by the photodetector 70 at the same time.

As described above, when the microneedle skin patch 10, in which the reaction layer 30 including enzyme reacting with the glycation products in the skin is formed, is attached to the skin, the glycation products 50 is absorbed into the reaction layer 30 of the patch 10 through the microneedle 20 and reacts with an enzyme component in the patch, and thus a change in the enzyme component in the patch occurs. Wavelengths and/or intensities of rays of light reflected at different physical quantities (e.g., reflexibility) according to concentrations of the changed enzyme component may be measured using the reaction detector, that is, the light source 60 and the photodetector 70, to calculate an amount of blood glucose.

However, in the conventional patch, in a process in which the light source 60 emits light and the photodetector 70 receives light, although there is a difference between the reflected light R1 reflected by the portion 31 in which the microneedle is disposed and the reflected light R2 reflected by the portion 32 in which the microneedle is not disposed, a change in the concentration (or color) of the reaction layer 30 may not be accurately measured because the photodetector 70 detects a result of a sum of two rays of the reflected light R1 and R2.

Figure 6:
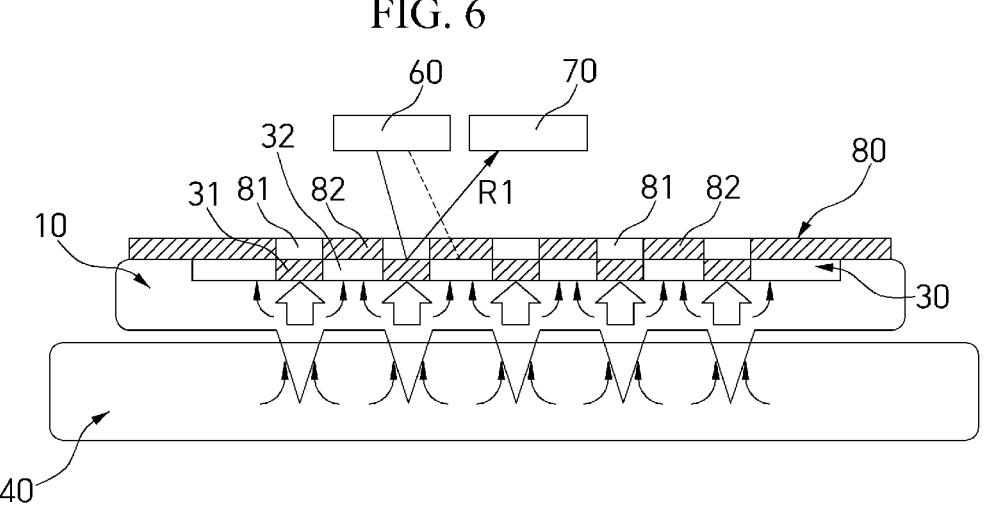
FIG. 6 is a view for describing a structure and an operation of a microneedle patch to which an optical trap according to the present invention is applied.

FIG. 6 is a view for describing a structure and an operation of a microneedle patch to which an optical trap according to the present invention is applied to solve the problem of the conventional patch 10.

When compared to the structure of FIG. 5, an optical trap 80 is disposed on a reaction layer 30 of a patch 10 to be positioned between a reaction detector (i.e., a light source 60 and a photodetector 70) and the reaction layer 30. In the optical trap 80, light passing parts 81 are formed at positions corresponding to portions 31 in which microneedles of the patch 10 are disposed to allow reflected light R1 to pass therethrough, and light blocking parts 82 are disposed at positions corresponding to portions 32 in which the microneedles are not disposed to absorb or scatter reflected light R2 so as to prevent the reflected light R2 from arriving on the photodetector 70.

Conversely, according to a design, the light blocking parts may also be formed at positions corresponding to the portions 31 in which the microneedles are disposed to block the reflected light R1, and the light passing parts may also be formed at positions corresponding to the portions 32 in which the microneedles are not disposed to allow the reflected light R2 to pass therethrough and arrive on the photodetector 70.

To make the light passing parts 81 of the optical trap 80, holes may be formed in an opaque substrate and may be filled with a light passing material to form the light passing parts 81. Alternatively, an upper surface and/or lower surface of a transparent substrate excluding the light passing parts 81 may be coated with a light blocking material (for example, light absorbing material or light scattering material) to form the light blocking parts 82.

According to the present invention, when the minimally invasive microneedle patch for reducing fear and pain while measuring blood glucose is used, since a degree of reaction of glycation products can be uniformly measured, an error in blood glucose calculation can be greatly reduced.

Although the present invention has been described in detail through the exemplary embodiments, it will be understood by those skilled in the art that the invention may be performed in specific forms different from the content disclosed in the present specification without changing the technological scope and essential features. The above-described embodiments should be considered as only examples in all aspects and not for purposes of limitation. In addition, it should be interpreted that the scope of the present invention is defined not by the detailed description but by the appended claims and encompasses all modifications and alterations derived from the scope and equivalents of the appended claims.

What is claimed is:

1. A skin patch for measuring blood glucose, comprising:

a patch comprising a skin attachment surface, a reaction layer which reacts with glycation products of skin, and a plurality of microneedles disposed on the skin attachment surface to guide the glycation products of the skin to the reaction layer; and an optical trap disposed on the reaction layer, the optical trap allowing light, which is reflected by only one portion among a portion in which a microneedle of the plurality of microneedles is disposed and a portion in which the microneedle is not disposed when the light is emitted to the reaction layer, to pass therethrough, wherein the optical trap is on an upper surface of the patch opposite the skin attachment surface, and separated from the plurality of microneedles by a body of the patch between the upper surface and the skin attachment surface;

wherein the optical trap and the reaction layer extend across the plurality of microneedles in a direction orthogonal to a projection direction of the plurality of microneedles; and wherein the optical trap comprises light passing parts which allow light to pass therethrough, and light blocking parts which block light, and the light passing parts and the light blocking parts alternate in a planar pattern, wherein the light passing parts and the light blocking parts are in contact with the upper surface of the reaction layer, and wherein each of the light passing parts aligns in the direction orthogonal to the projection direction of the plurality of microneedles with a corresponding microneedle of the plurality of microneedles and with one of first portions of the reaction layer having a concentration of the reactant expressed to be darker than a concentration of the reactant in second portions of the reaction layer, and each of the light blocking parts aligns in the direction orthogonal to the projection direction of the plurality of microneedles with one of the second portions of the reaction layer and with a portion of the skin attachment surface that extends across a space between a pair of adjacent microneedles, wherein the reaction layer is at least partly within the body of the patch, and the optical trap is outside the body of the patch and in direct contact with an upper surface of the reaction layer.

2. The skin patch of claim 1, wherein:

the light passing parts allow light reflected by the portion, in which the microneedle is disposed, to pass therethrough; and the light blocking parts block light reflected by the portion in which the microneedle is not disposed.

3. The skin patch of claim 2, wherein a material of the optical trap is an opaque substrate and the light passing parts are holes formed in the opaque substrate and filled with a light passing material.

4. The skin patch of claim 2, wherein a material of the optical trap is a transparent substrate and the light blocking parts comprise a light blocking material applied on a surface of the transparent substrate.

5. The skin patch of claim 1, wherein:

the light blocking parts block light reflected by the portion in which the microneedle is disposed; and the light passing parts allow light reflected by the portion in which the microneedle is not disposed to pass therethrough.

6. The skin patch of claim 5, wherein a material of the optical trap is an opaque substrate and the light passing parts are holes formed in the opaque substrate and filled with a light passing material.

7. The skin patch of claim 5, wherein a material of the optical trap is a transparent substrate and the light blocking parts comprise a light blocking material applied on a surface of the transparent substrate.

8. A blood glucose measuring apparatus comprising:

a patch comprising a skin attachment surface, a reaction layer which reacts with glycation products of skin, and a plurality of microneedles disposed on the skin attachment surface to guide the glycation products of the skin to the reaction layer;

a reaction detector which emits light to the reaction layer and receives light reflected by the reaction layer to detect reactivity of the glycation products; and an optical trap disposed on the reaction layer, the optical trap allowing only one ray of light to pass therethrough and arrive on the reaction detector, wherein the only one ray of light is reflected by the reaction layer of the patch and is one of light reflected by a portion in which a microneedle of the plurality of microneedles is disposed and light reflected by a portion in which the microneedle is not disposed, wherein the optical trap is on an upper surface of the patch opposite the skin attachment surface, and separated from the plurality of microneedles by a body of the patch between the upper surface and the skin attachment surface;

wherein the optical trap and the reaction layer extend across the plurality of microneedles in a direction orthogonal to a projection direction of the plurality of microneedles; and wherein the optical trap comprises light passing parts which allow light to pass therethrough, and light blocking parts which block light, and the light passing parts and the light blocking parts alternate in a planar pattern, wherein the light passing parts and the light blocking parts are in contact with the upper surface of the reaction layer, and wherein each of the light passing parts aligns in the direction orthogonal to the projection direction of the plurality of microneedles with a corresponding microneedle of the plurality of microneedles and with one of first portions of the reaction layer having a concentration of the reactant expressed to be darker than a concentration of the reactant in second portions of the reaction layer, and each of the light blocking parts aligns in the direction orthogonal to the projection direction of the plurality of microneedles with one of the second portions of the reaction layer and with a portion of the skin attachment surface that extends across a space between a pair of adjacent microneedles, and wherein the reaction layer is at least partly within the body of the patch, and the optical trap is outside the body of the patch and in direct contact with an upper surface of the reaction layer.

9. The blood glucose measuring apparatus of claim 8, wherein:

the light passing parts allows the light reflected by the portion, in which the microneedle is disposed, to pass therethrough and arrive on the reaction detector; and the light blocking parts blocks the light reflected by the portion in which the microneedle is not disposed not to arrive on the reaction detector.

10. The blood glucose measuring apparatus of claim 8, wherein:

the light blocking parts blocks the light reflected by the portion, in which the microneedle is disposed, not to arrive on the reaction detector; and the light passing parts allows the light reflected by the portion in which the microneedle is not disposed to pass therethrough and arrive on the reaction detector.

\* \* \* \* \*